United States Patent
Tseng et al.

(10) Patent No.: US 8,144,887 B2
(45) Date of Patent: *Mar. 27, 2012

(54) ELECTRONIC STETHOSCOPE AND THE STETHOSCOPE AUSCULTATION METHOD USING THE SAME

(75) Inventors: Kuo-Hua Tseng, Yilan County (TW); Yu-Kon Chou, Taipei County (TW); Yii-Tay Chiou, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 296 days.

This patent is subject to a terminal disclaimer.

(21) Appl. No.: 12/147,751

(22) Filed: Jun. 27, 2008

(65) Prior Publication Data

US 2009/0232322 A1 Sep. 17, 2009

(30) Foreign Application Priority Data

Mar. 12, 2008 (TW) ............................... 97108608 A

(51) Int. Cl.
*A61B 7/04* (2006.01)
(52) U.S. Cl. ........................ 381/67; 381/71.13; 381/74
(58) Field of Classification Search ............... 381/67, 381/71.6, 71.7, 71.13, 72, 309, 81, 74, 332, 381/107, 370, 376, 381; 434/266, 262, 267, 434/270, 307, 318, 365, 396; 327/141, 297; 335/206, 341, 20; 600/559
See application file for complete search history.

(56) References Cited

U.S. PATENT DOCUMENTS

| | | | |
|---|---|---|---|
| 3,227,836 A * | 1/1966 | Renwick, Sr. | ......... 200/61.58 R |
| 4,534,058 A | 8/1985 | Hower | |
| 5,238,001 A | 8/1993 | Gallant et al. | |
| 5,539,831 A * | 7/1996 | Harley | ............................ 381/67 |

(Continued)

FOREIGN PATENT DOCUMENTS

TW 558434 10/2003

OTHER PUBLICATIONS

Taiwan Intellectual Property Office, "Office Action", Aug. 9, 2011, Taiwan.

*Primary Examiner* — Vivian Chin
*Assistant Examiner* — Leshui Zhang
(74) *Attorney, Agent, or Firm* — WPAT, PC; Justin King

(57) ABSTRACT

The present invention relates to a stethoscope auscultation method, adapted for an improved stethoscope so as to be used for assisting a medical diagnosis according to visceral sounds. The stethoscope auscultation method comprises the steps of: providing a stethoscope, whereas the stethoscope is composed of a stethoscope head module, a processing unit and a signal output unit, and the stethoscope head module further comprises a sensor and a visceral sound receiver; enabling the sensor to issue an activation signal to the processing unit as soon as it detects that the stethoscope head module enters an auscultation mode, and thereby activating the stethoscope; using the stethoscope to perform an auscultation process upon a living body as the visceral sound receiver is enabled to obtain audio signals originated from the visceral organs of the living body; enabling the processing unit to shut off the stethoscope automatically when the visceral sound receiver is unable to obtain the audio signals originated from the visceral organs for environmental purposes, such as reducing power consumption of the stethoscope, prolonging lifespan of the battery used in the stethoscope.

21 Claims, 4 Drawing Sheets

U.S. PATENT DOCUMENTS

| | | |
|---|---|---|
| 5,568,814 A | 10/1996 | Gallant et al. |
| 5,692,513 A | 12/1997 | Davis et al. |
| 5,737,429 A | 4/1998 | Lee |
| 5,764,776 A | 6/1998 | Francais |
| 5,812,678 A | 9/1998 | Scalise et al. |
| 5,913,834 A | 6/1999 | Francais |
| 6,082,367 A | 7/2000 | Greeninger et al. |
| 6,168,568 B1 | 1/2001 | Gavriely |
| 6,210,344 B1 | 4/2001 | Perin et al. |
| 6,219,424 B1 | 4/2001 | Murphy |
| 6,220,866 B1 * | 4/2001 | Amend et al. ................ 434/266 |
| 6,228,040 B1 | 5/2001 | Craine |
| 6,247,474 B1 | 6/2001 | Greeninger et al. |
| 6,498,854 B1 | 12/2002 | Smith |
| 6,533,736 B1 | 3/2003 | Moore |
| 6,661,897 B2 | 12/2003 | Smith |
| 2003/0002685 A1 * | 1/2003 | Werblud .......................... 381/67 |
| 2003/0128847 A1 * | 7/2003 | Smith ............................. 381/67 |
| 2004/0105556 A1 * | 6/2004 | Grove ............................. 381/67 |

\* cited by examiner

US 8,144,887 B2

ELECTRONIC STETHOSCOPE AND THE STETHOSCOPE AUSCULTATION METHOD USING THE SAME

FIELD OF THE INVENTION

The present invention relates to an electronic stethoscope and a stethoscope auscultation method using the same, and more particularly, to an auscultation method and apparatus designed with energy-conservation ability for reducing power consumption while prolonging battery lifespan used in the apparatus.

BACKGROUND OF THE INVENTION

Analysis of heart, lung and vascular disorders by means of noninvasive auscultation has long been a very useful tool for medical diagnosis of ailments. Conventional electronic stethoscopes had not been invented until the Year 1922. Modern electronic stethoscopes can improve sound quality and provide a visual indication of heart sounds or chest sounds, such as cardiophonography. However, early electronic stethoscopes, which are composed of vacuum tubes or transistors, were typically more expensive and bulkier than conventional stethoscopes. Accordingly, electronic stethoscopes can only begin to replace the dominant role of conventional stethoscopes after the rapid development of IC technology at the end of $20^{th}$ century. Nevertheless, there were many electronic stethoscopes currently available on the market, which can be divided into two categories, i.e. the analog electronic stethoscopes and the digital electronic stethoscope, whereas most of which are analog electronic stethoscopes.

Compared with conventional stethoscopes, the electronic stethoscope, despite its advantages, and disadvantageous, is more expensive and requires certain practice for those who have been accustomed to the operation of conventional stethoscopes, and moreover, its operation is often limited by its battery capacity and thus requires a battery change from time to time. Accordingly, although it is becoming popular nowadays, the electronic stethoscope still can not replace the conventional stethoscope completely.

In a prior-art auscultation device disclosed in U.S. Pub. No. 4,534,058, entitled "Electronic stethoscope with automatic power shut-off", the electronic stethoscope is designed with a shut-off circuit that enables the stethoscope to shut off and enter a power-saving mode after the stethoscope is detected to be inactive for a specific period of time. The aforesaid automatic power shut-off is already common in most conventional electronic stethoscope currently available on the market, however it has shortcomings listed as follows:
(1) Any electronic stethoscope with automatic power shut-off will have to wait for the specific period of time until it can be shut off and can not be shut off immediately after it is inactive such that there is power being wasted during the waiting.
(2) The operation of a conventional electronic stethoscope is limited by its battery capacity and thus requires a battery change from time to time so as to prevent the battery from running out in the middle of an auscultation process.
(3) Any electronic stethoscope that requires constant battery change so as to sustain a normal operation is not only costly, but also is not environmental friendly.
(4) Any medical personnel who wants to use the aforesaid electronic stethoscope with such automatic power shut-off that is inactive will have to start it by pressing a button or a switch which is inconvenient and time-consuming.

Therefore, there is a need for an electronic stethoscope that is designed with environmental protection and energy-conservation capabilities for reducing power consumption while prolonging the lifespan of the battery used in the apparatus.

SUMMARY OF THE INVENTION

The object of the present invention is to provide an electronic stethoscope and the stethoscope auscultation method using the same with energy-conservation ability for reducing its power consumption while prolonging the lifespan of the battery used in the electronic stethoscope.

To achieve the above object, the present invention provides a stethoscope auscultation method, adapted for an improved stethoscope so as to be used for assisting a medical diagnosis according to visceral sounds, comprising the steps of: providing a stethoscope, whereas the stethoscope is composed of a stethoscope head module, a processing unit and a signal output unit, and the stethoscope head module further comprises a sensor and a visceral sound receiver; enabling the sensor to issue an activation signal as soon as it detects that the stethoscope head module enters an auscultation mode; activating the stethoscope as soon as the activation signal is received by the processing unit; using the stethoscope to perform an auscultation process upon a living body as the visceral sound receiver is enabled to obtain audio signals originating from the visceral organs of the living body; enabling the processing unit to shut off the stethoscope automatically when the visceral sound receiver is unable to obtain the audio signals originated from the visceral organs.

Moreover, to achieve the above object, the present invention further provides a stethoscope adapted for obtaining audio signals originated from visceral organs of a living body, comprising: a stethoscope head module, configured with a sensor and a visceral sound receiver in a manner that the sensor is designed to issue an activation signal as soon as it detects that the stethoscope head module enters an auscultation mode and the visceral sound receiver is used for obtaining the audio signals originated from the visceral organs of the living body; a processing unit, for processing the received audio signals of the visceral organs; and a signal output unit, for outputting the audio signals.

Further the scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as follows.

Figure 1:
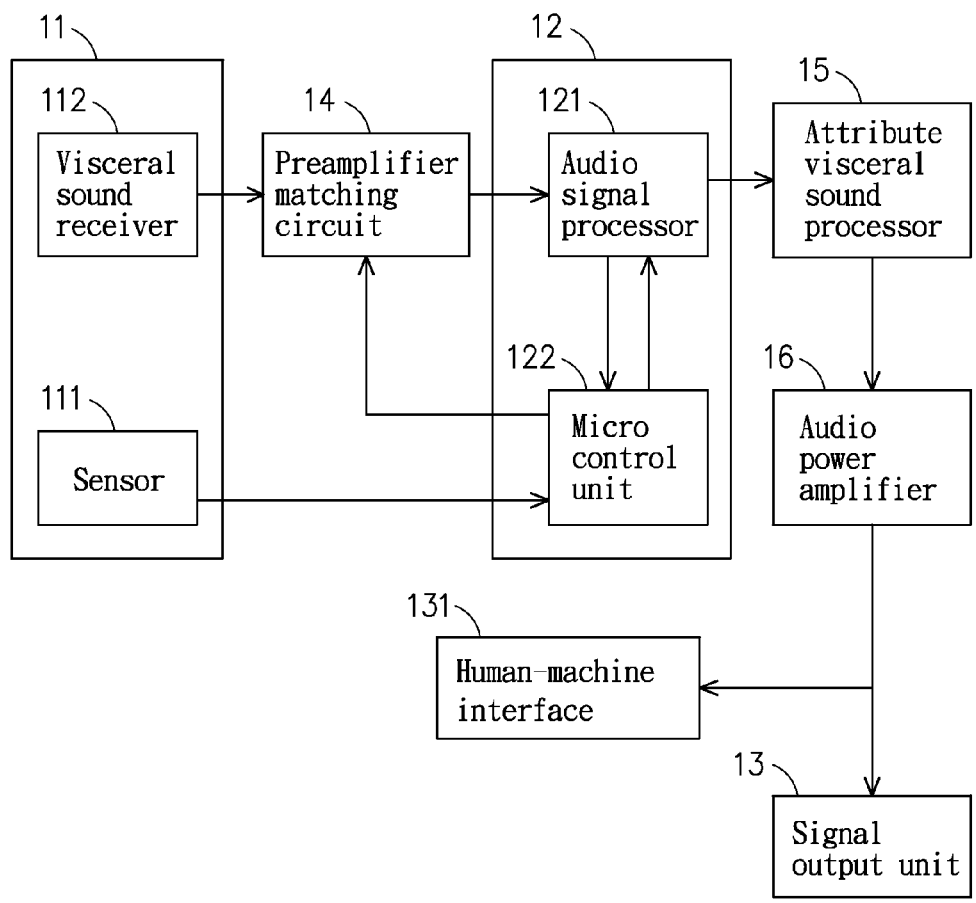
FIG. 1 is a block diagram of a stethoscope of the invention.

Please refer to FIG. 1, which is a block diagram of a stethoscope of the invention. The stethoscope 10 of FIG. 1 is adapted for obtaining audio signals originating from visceral organs of a living body, such as heat sounds, lung sounds, gastrointestinal sound originated from the active heart, lung, stomach and intestines of a living body. The stethoscope 10 comprises: a stethoscope head module 11, a processing unit 12 and a signal output unit 13; in which the stethoscope head module 11, being the part of the stethoscope 10, physically contacts the living body, and is further composed of a sensor 111 and a visceral sound receiver 112. The sensor 111 is used for detecting whether or not the stethoscope 10 is in an auscultation mode, and the visceral sound receiver 112 is used for obtaining audio signals originated from visceral organs of the living body. Moreover, the manner relating to how to use the sensor 111 to detect whether or not the stethoscope 10 is in the auscultation mode will be described hereinafter.

The processing unit 12, which is composed of an audio signal processor 121 and a micro control unit 122 are used for processing the received audio signals of visceral organs. Wherein, the audio signal processor 121, being electrically connected to the visceral sound receiver 112 and the micro control unit 122, is used for determining whether the visceral sound receiver 112 is receiving visceral sounds in a continuous manner and further is designed to issue a shut-off signal as soon as the visceral sound receiver 112 receives no visceral sound. In an exemplary embodiment, the audio signal processor 121 can be a digital signal processing (DSP) audio signal processor. Moreover, the micro control unit 122, being electrically connected to the sensor 111 and the audio signal processor 121, is enabled to receive the activation signal and the shut-off signal respectively from the sensor 111 and the audio signal processor 121 so that it is able to turn on the stethoscope 10 as soon as the activation signal is received thereby, or it is able to turn off the stethoscope 10 as soon as the shut-off signal is received thereby.

In this embodiment, there is a preamplifier matching circuit 14 arranged at a position between the visceral sound receiver 112 and the audio signal processor 121, which is used for amplifying the audio signal received from the visceral sound receiver 112 and then feeds the amplified audio signal to the audio signal processor 121 for processing. In addition, the signal output unit 13 is designed to be electrically connected to the processing unit 12, there can be an attribute visceral sound processor 15 and an audio power amplifier 16 being arranged between the signal output unit 13 and the processing unit 12, in that the attribute visceral sound processor 15 is electrically connected to the audio signal processor 121 to be used for amplifying a characteristic band contained in the received audio signals of the visceral organs, and the audio power amplifier 16 is used for amplifying the audio signals of the visceral organs after they are processed by the attribute visceral sound processor 15 while feeding the amplified audio signal to the signal unit 13 for outputting. It is noted that the aforesaid preamplifier matching circuit 14, the attribute visceral sound processor 15 and the audio power amplifier can all be integrated into the processing unit 12 as required.

In most cases, the signal output unit 13 can be an earpiece so that it can be inserted in the ears of the stethoscope's operator. Moreover, the signal output unit 13 can be connected to an human-machine interface 131 so as to displaying information relating to the audio signals detected by the stethoscope 10 on the human-machine interface 131. For instance, if the stethoscope 10 is used for detecting heart sound, the waveforms of the heart sound as well as its frequency and amount of heart beats per minute can be shown on the human-machine interface 131.

Figure 2:
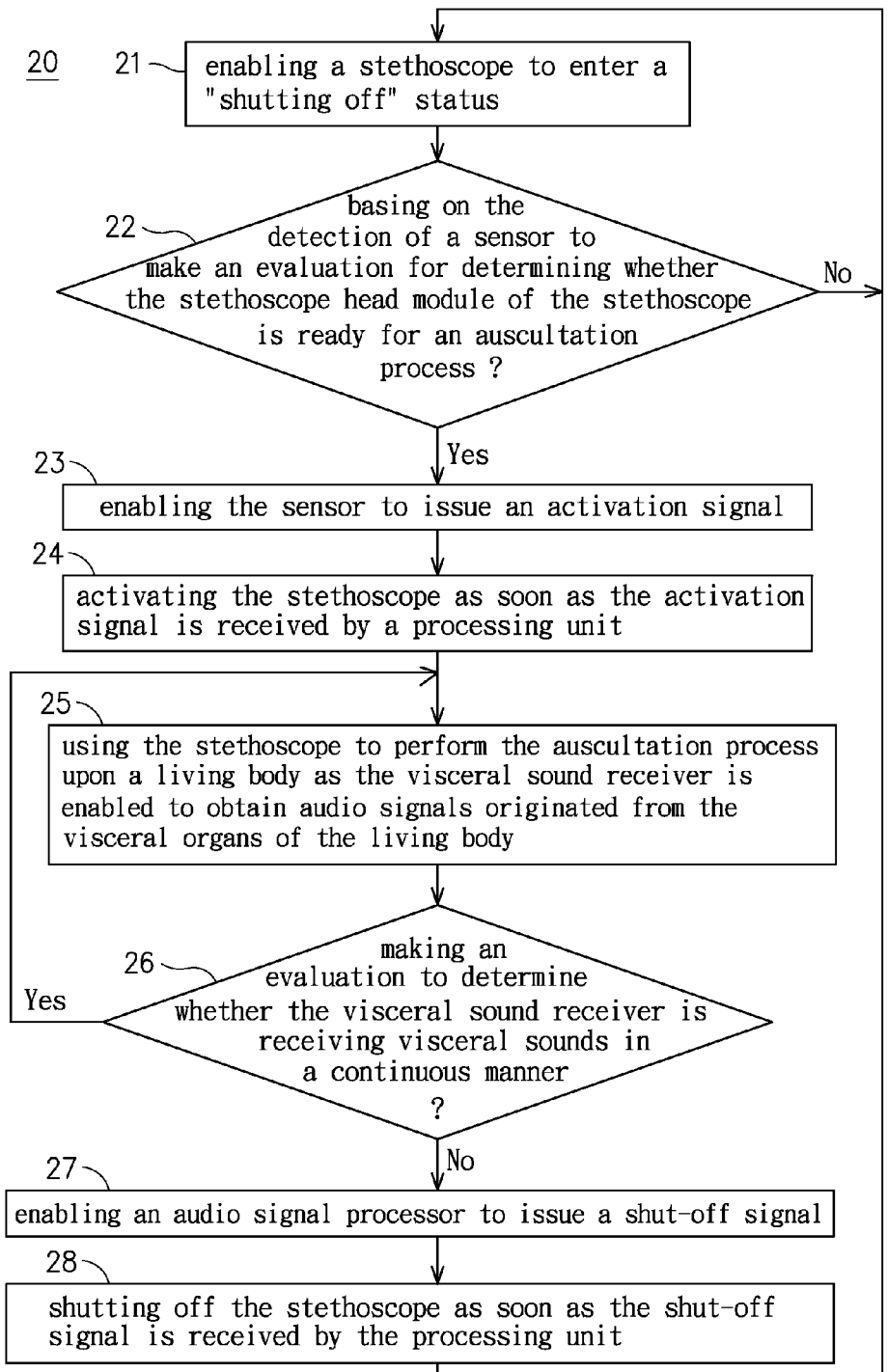
FIG. 2 is a flow chat depicting steps of the stethoscope auscultation method according to the present invention.

Please refer to FIG. 2, which is a flow chat depicting steps of the stethoscope auscultation method according to the present invention. The operation of the stethoscope shown in FIG. 1 is depicted in the flow chart of FIG. 2 in a step by step manner, which will be described in the following:

Step 21: enabling the stethoscope 10 to enter a "shutting off" status; whereas the "shutting off" is similar to enable the stethoscope 10 to enter a waiting mode without terminating electricity to the stethoscope 10;

Step 22: based on the detection of the sensor 111 to make an evaluation for the stethoscope head, module 11 of the stethoscope 10 provides signals to makes an evaluation to determine whether of not the stethoscope head module 11 is ready for an auscultation process; if so, then the flow proceeds to step 23; otherwise, the flow proceeds back to step 21;

Step 23: enabling the sensor 111 to issue an activation signal to the processing unit 12;

Step 24: activating the stethoscope 10 as soon as the activation signal is received by the processing unit 12; whereas the processing unit 12 is configured with a micro control unit 122 so that the micro control unit 122 is the one usually being used for receiving the activation signal and thus activating the stethoscope 10 accordingly;

Step 25: using the stethoscope 10 to perform the auscultation process upon a living body as the visceral sound receiver 112 is enabled to obtain audio signals originated from the visceral organs of the living body;

Step 26: making an evaluation to determine whether the visceral sound receiver 112 is receiving visceral sounds in a continuous manner; if so, the flow proceeds back to step 25 since the stethoscope head module 11 is still in contact with the living body and the auscultation process is still in progress; otherwise, the flow proceeds to step 27 since the stethoscope head module 11 is no longer in contact with the living body and the auscultation process is stopped;

Step 27: as the discontinuity of visceral sound in the visceral sound receiver 112 will cause the terminating of audio signals being received by the audio signal processor 121, the audio signal processor 121 is enabled to issue a shut-off signal; whereas the duration of the terminating can be defined by a software control or hardware control, e.g. in an exemplary embodiment, the audio signal processor is defined to wait for the audio signal for a period between 3 to 5 sec and the issue the shut-off signal if no audio signal is received during the waiting period, by that the unintentional shutting-off of the stethoscope 10, caused by the temporary separation of the stethoscope 10 from the living body as it is moved from place to place in the auscultation process, can be prevented;

Step 28: using the processing unit 12 to shut off the stethoscope 10 as soon as the shut-off signal is received thereby;

and similarly, as the processing unit 12 is configured with a micro control unit 122 so that the micro control unit 122 is the one usually being used for receiving the shut-off signal and thus shutting off the stethoscope 10 accordingly.

Figure 3:
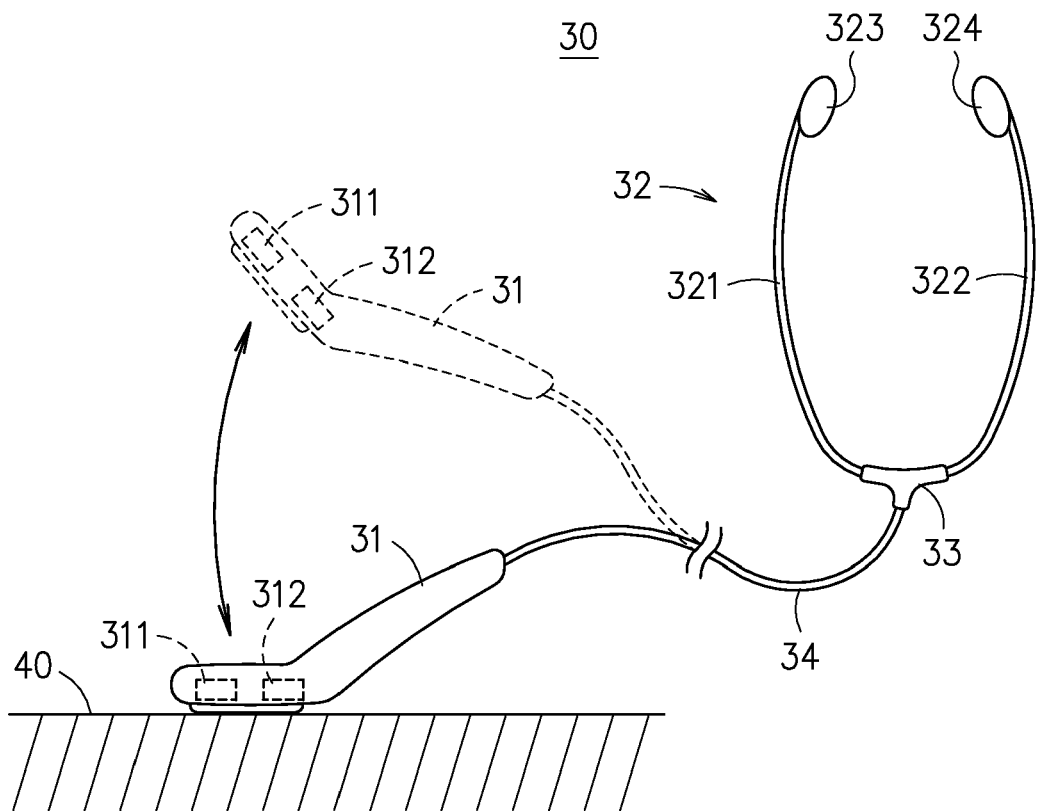
FIG. 3 shows the operation of a sensor in a stethoscope of the invention.

Please refer to FIG. 3, which shows the operation of a sensor in a stethoscope of the invention. The stethoscope 30 comprises a stethoscope head module 31 and a ear hook 32; in which the stethoscope head module 31, being a device similar to the stethoscope head module 11 shown in FIG. 1 and being the part physically contacting with a living body, is further composed of a sensor 311 and a visceral sound receiver 312. The sensor 311 is used for detecting whether or not the stethoscope 30 is in an auscultation mode, and the visceral sound receiver 312 is used for obtaining audio signals originated from visceral organs of the living body. Moreover, the ear hook 32 has two symmetrically arranged supporting parts 321, 322, both of which respectively having earpieces 323, 324 attached to the top thereof. It is noted that the earpieces 323, 324 are substantially the signal output unit 13 of FIG. 1. In FIG. 3, the two supporting part 321, 322 is connected at the bottom thereof by the use of a connecting part 33. Generally, the two supporting parts 321, 322 are designed to be elastic for enabling the two to be pull apart from each other while subjecting to an external force and to spring back to its original position while being released from the external pulling force. Thereby, the connecting part 33 can be made of a soft rubber. Operationally, the user can wear the ear hook on his/her neck when the stethoscope 30 is not being used, and when the stethoscope 30 is required for an auscultation process, the user can simply first pull the two supporting parts 321, 322 apart and then fit the earpieces 323, 324 in his/her ears while picking up the stethoscope head module 31 disposed on any surface 40 for processing the auscultation process. In this embodiment, the stethoscope 30 is a wired device as the stethoscope head module 31 and the ear hook 32 is connected by the use of a connecting cable 34. Nevertheless, it is noted that the stethoscope head module 31 and the ear hook 32 can be connected by the use of a wireless means.

When a stethoscope is used in an auscultation process, its stethoscope head module which was placed on a desktop or hanging on its user's chest will be picked up and then have physical contact with a patient, whereas the moving of the stethoscope head module will be detected by the sensor and thus enable the stethoscope to enter the auscultation mode. In this embodiment, the moving as well as the raising of the stethoscope head module 31 will be detected by the sensor 311, which can be a device selected from the group consisting: a vibration sensor, an accelerometer, an angular velocity sensor, an angle sensor, a pressure sensor, an optical sensor, and the combinations thereof. When a vibration sensor is selected to be the sensor 311, the vibration of the stethoscope head module 31 is measured and compared with a threshold value so as to determine whether the stethoscope head module 31 is in the auscultation mode based on the comparison. That is, if the measured vibration is smaller than a threshold value, it represents that the stethoscope head module 31 might just be subjected to some minor bumping and is not being used in an auscultation process. On the other hand, when the measured vibration is larger than the threshold value, it represents the stethoscope head module 31 to be in an auscultation mode so that the sensor 311 is enabled to issue an activation signal for preparing the visceral sound receiver 312 to receive visceral sounds originating from visceral organs of a living body. However, as soon as the stethoscope head module 31 is separated from the living body and thus the visceral sound receiver 312 is no longer able to receive any visceral sound, the stethoscope 30 is shut off.

When an accelerometer is selected to be the sensor 311, the acceleration variation of the stethoscope head module 31 is measured and compared with a threshold value so as to determine whether the stethoscope head module 31 is in an auscultation mode based on the comparison. In addition, when an angular velocity is selected to be detected by the sensor 311, the inclination variation of the stethoscope head module 31, i.e. the angle variation of the stethoscope head module 31 as it is being moved, is measured and compared with a threshold value so as to determine whether the stethoscope head module 31 is in the auscultation mode based on the comparison. Moreover, when an angle detection is selected to be the sensor 311, an inclination angle of the stethoscope head module 31 placed on a surface 40 with reference to a reference position is measured and compared with a threshold value so as to determine whether the stethoscope head module 31 is in the auscultation mode basing on the comparison. Furthermore, when a pressure sensor is selected to be the sensor 311, the pressure variation of the stethoscope head module 31 is measured and compared with a threshold value so as to determine whether the stethoscope head module 31 is in the auscultation mode based on the comparison. That is, since the pressure of the stethoscope head module 31 as it is being place idly on a surface 40 is different from that when it is being used in an auscultation process, the pressure difference can be used as the basis for determining whether the stethoscope 30 is in the auscultation mode.

Figure 4:
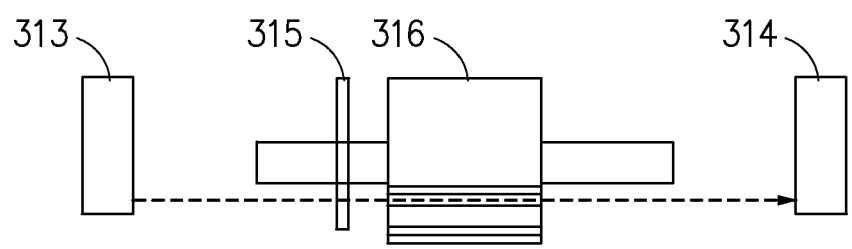
FIG. 4 shows the structure of an optical sensor adapted for a stethoscope of the invention.

In addition, when an optical sensor is selected to be the sensor 311 and the optical sensor, is the one shown in FIG. 4, comprising a light emitter 313, a light receiver 314, a light grating 315 and a roller 316, being configured in a manner that a beam emitted from the light emitter 313 is received by the light receiver 314 as the light receiver 314 is arranged at a position corresponding to that of the light emitter 313, and a light grating 315 is connected with the roller 316 while placing the two at a position between the light emitter 313 and the light receiver 314 for enabling the light grating 315, being controlled by the driven of the roller 316 so that it is brought along to move with the movement of the stethoscope head module 31, to allow/block light emanating from the light emitter 313 to pass therethrough, the continuity of light is measured by the optical sensor 311 so as to determine whether the stethoscope head module 31 is in the auscultation mode based on continuity measurement. That is, the continuity measurement of the light being received by the light receiver 314 is sent to the micro control unit 122 shown in FIG. 1 to be used thereby for evaluating the movement of the stethoscope head module 31 and thus determining whether the stethoscope head module 31 is in the auscultation mode based on the evaluation.

Figure 5:
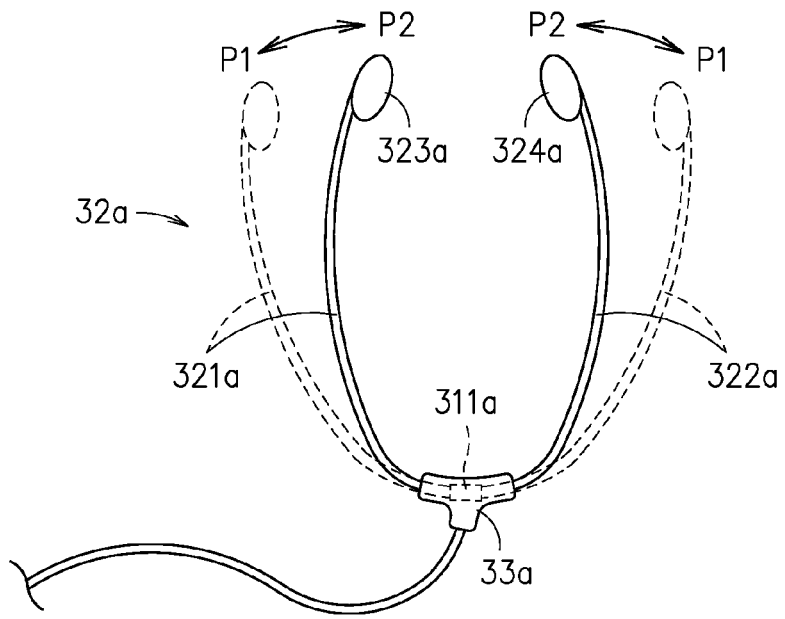
FIG. 5 shows the operation of another sensor in the stethoscope of the invention.

In FIG. 5, the ear hook 32a, which is structured similar to the ear hood 32 of FIG. 3, also comprises two supporting parts 321a, 322a, whereas both of which are also having ear pieces 323a, 324a attached to the top thereof. In FIG. 5, the two supporting part 321a, 322a is connected at the bottom thereof by the use of a connecting part 33a in a manner that the two supporting parts 321a, 322a can be positioned as a first pose P1 by pulling the two apart from each other, or can be positioned as a second pose P2 by drawing the two close to each other. It is noted that there can be a sensor 311a being disposed at the joint of the two supporting parts, i.e. embedded in the connecting part 33a, in a manner that the sensor 311a is turned on/off according to whether the two supporting parts is positioned as the first/second poses. The sensor 311a can be a contact switch, a pressure sensor, a stress sensor or the combinations thereof. In an exemplary embodiment, when the two supporting parts 321a, 322a is positioned as the first pose P1, the sensor 311a is turned on indicating that the ear hook 32 is being fitted into the ears of an user and thus the sensor 311 which can be a contact switch will then issue an activation signal for preparing the stethoscope for an auscultation process; and when the two supporting parts 321a, 322a is positioned as the second pose P2, the at least one sensor is turned off indicating that the ear hook 32a is being removed from the ears of the user and thus the sensor 311a will shut off the stethoscope 30 for power saving.

Figure 6:
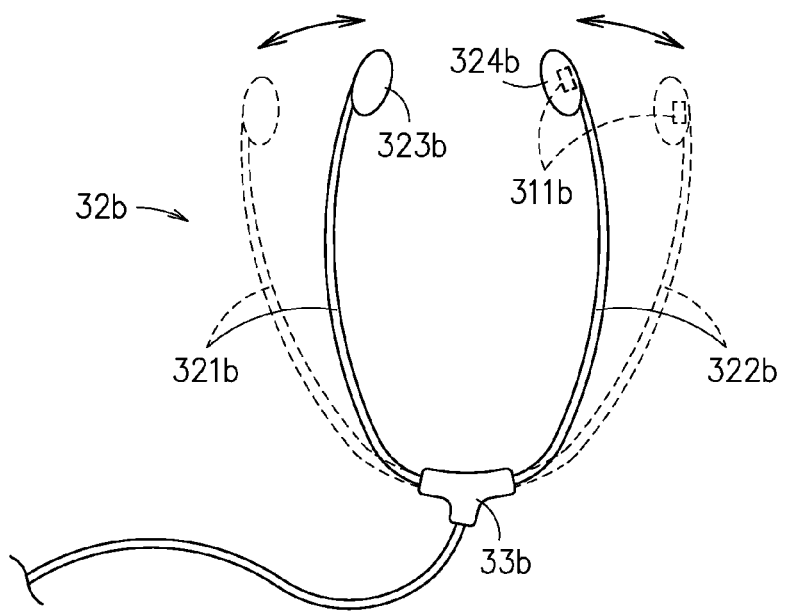
FIG. 6 shows the operation of yet another sensor in a stethoscope of the invention.

In FIG. 6, the ear hook 32b, which is also structured similar to the ear hood 32 of FIG. 3, also comprises two supporting parts 321b, 322b, whereas both of which are also having ear pieces 323b, 324b attached to the top thereof. In FIG. 6, the two supporting part 321b, 322b is connected at the bottom thereof by the use of a connecting part 33b. The aforesaid embodiment is characterized in that: at least one of the two earpieces 323b, 324b is fitted with a pressure sensor 311b therein to be used for detecting pressure variation of the earpiece; and when the earpiece embedded with the pressure sensor 311b is inserted inside an ear of a user, pressure variation will be detected by the pressure sensor 311b and then is compared with a threshold value so as to determine whether the stethoscope head module 31 is in the auscultation mode basing on the comparison. Normally, when the measured pressure variation is larger than the threshold value, the stethoscope head module 31 is determined to be in the auscultation mode; and when the measured pressure variation is smaller than the threshold value, it is determined that the auscultation process is completed and thus the sensor 311b will shut off the stethoscope 30 for power saving.

In the embodiments shown in FIG. 5 and FIG. 6, the powering of the stethoscope 30 is determined based on whether the ear hooks 32a, 32b are being worn by users, so that it can save the user from the trouble of manually turn on and off the stethoscope repetitively and thus stethoscope of the invention is not only more user friendly as those conventional stethoscope, but also is more power efficient.

To sum up, the electronic stethoscope of the invention is more power efficient since by the stethoscope auscultation method provided in the invention, it can be shut off automatically as soon as there is an termination is visceral sound receiving and can be reactivated by enabling the sensor to issue an activation signal as soon as the sensor detects that the stethoscope enters an auscultation mode. Thereby, the power consumption of the stethoscope can be reduced so as to prolong the lifespan of the battery used in the stethoscope, and thus doctors can make a diagnosis with less effort and time, since he/she can perform an auscultation process fluently without having to stop to replace a battery. In an experiment using two AAA batteries and assuming each patient will take three minutes to complete an auscultation process, a conventional electronic stethoscope can be used for diagnosing only 60 patients, but the electronic stethoscope of the invention can be used for at least 240 patients without battery changing. This suggests that the power efficiency of the electronic stethoscope is improved at least four times that of a conventional electronic stethoscope.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A stethoscope auscultation method, adapted for assisting a medical diagnosis according to visceral sounds, comprising the steps of:

providing a stethoscope, whereas the stethoscope is comprised of:
  a stethoscope head module comprising:
    at least a first sensor, for detecting whether or not the stethoscope is ready for entering an auscultation mode, and a visceral sound receiver, for receiving audio signals of visceral organs originating from visceral organs of a living body;
  at least two supporting parts, for positioning the stethoscope in multiple poses, each supporting part comprising:
    an earpiece positioned to the top thereof, fitted with at least a second sensor embedded in the earpiece for sensing pressure variations of the earpiece;
  a joint of the at least two supporting parts, for joining the two supporting parts together, comprising at least a third sensor for detecting the multiple poses of the stethoscope;
  a preamplifier matching circuit, electrically connected to the stethoscope head module, for amplifying the received audio signals of the visceral organs;
  a processing unit electrically connected to the preamplifier matching circuit for processing the received audio signals of the visceral organs and controlling overall operation of the stethoscope, comprising:
    an audio signal processor, electrically connected to the visceral sound receiver, for processing the received audio signals of the visceral organs and issuing a shut-off signal as soon as the visceral sound receiver receives no visceral sound; and
    a micro control unit, electrically connected to the sensors, the preamplifier matching circuit, and the audio signal processor, being designed to receive the activation signal and the shut-off signal so as to perform one action selected from the group consisting: turning on the stethoscope according to the activation signal and shutting off the stethoscope according to the shut-off signal;
  an attribute visceral sound processor, electrically connected to the processing unit, for receiving and amplifying a characteristic band of the visceral organs contained in the received audio signals;
  an audio power amplifier, electrically connected to the attribute visceral sound processor, for amplifying the audio signals of the visceral organs after they are processed by the attribute visceral sound processor; and
  a signal output unit, electrically connected to the audio power amplifier for outputting the audio signals received from the audio power amplifier;
enabling the first sensor to issue a first activation signal to the processing unit as soon as it detects that the stethoscope head module enters the auscultation mode, and enabling the audio signal processor to issue a shut-off signal as soon as the visceral sound receiver receives no visceral sound;
enabling the second sensor to issue a second activation signal to the processing unit upon evaluation of the sensed pressure variation to determine whether the stethoscope is ready for entering the auscultation mode;
enabling the third sensor to issue a third activation signal to the processing unit upon detection of a pose of the stethoscope indicating the stethoscope is ready for entering an auscultation mode;
activating the stethoscope as soon as the first activation signal is received by the processing unit;

using the stethoscope to perform an auscultation process upon the living body as the visceral sound receiver is enabled to receive the audio signals originated from the visceral organs of the living body;

amplifying and processing the received audio signals of the visceral organs received from the visceral sound receiver, and performing further signal processing by amplifying a characteristic band of the visceral organs contained in the received audio signals;

determining whether the visceral sound receiver is receiving the visceral sounds in a continuous manner, and if not, issuing the shut-off signal; and enabling the micro control unit of the processing unit to shut off the stethoscope automatically when the visceral sound receiver is unable to receive the audio signals originated from the visceral organs, when the comparison of the pressure variation of the second sensor indicates the stethoscope is not ready for entering the auscultation mode, or when the pose of the stethoscope sensed by the third sensor indicates the stethoscope is not ready for entering the auscultation mode.

2. The stethoscope auscultation method of claim 1, wherein at least one of the first sensor, the second sensor, and the third sensor is a device selected from the group consisting: a vibration sensor, an accelerometer, an angular velocity sensor, an angle sensor, a pressure sensor, an optical sensor, and the combinations thereof.

3. The stethoscope auscultation method of claim 2, wherein when the vibration sensor is selected to be at least one of the first sensor, the second sensor, and the third sensor, the vibration of the stethoscope head module is measured and compared with a threshold value so as to determine whether the stethoscope head module is in the auscultation mode basing on the comparison.

4. The stethoscope auscultation method of claim 2, wherein when the accelerometer is selected to be at least one of the first sensor, the second sensor, and the third sensor, the acceleration variation of the stethoscope head module is measured and compared with a threshold value so as to determine whether the stethoscope head module is in the auscultation mode basing on the comparison.

5. The stethoscope auscultation method of claim 2, wherein when the angular velocity is selected to be at least one of the first sensor, the second sensor, and the third sensor, the inclination variation of the stethoscope head module is measured and compared with a threshold value so as to determine whether the stethoscope head module is in the auscultation mode basing on the comparison.

6. The stethoscope auscultation method of claim 2, wherein when the angle sensor is selected to be at least one of the first sensor, the second sensor, and the third sensor, an inclination angle of the stethoscope head module with reference to a reference position is measured and compared with a threshold value so as to determine whether the stethoscope head module is in the auscultation mode basing on the comparison.

7. The stethoscope auscultation method of claim 2, wherein when the pressure sensor is selected to be at least one of the first sensor, the second sensor, and the third sensor, the pressure variation of the stethoscope head module is measured and compared with a threshold value so as to determine whether the stethoscope head module is in the auscultation mode basing on the comparison.

8. The stethoscope auscultation method of claim 2, wherein when the optical sensor is selected to be at least one of the first sensor, the second sensor, and the third sensor, the optical sensor comprises a light emitter, a light receiver, a light grating and a roller, being configured in a manner that a beam emitted from the light emitter is received by the light receiver as the light receiver is arranged at a position corresponding to that of the light emitter, and the light grating is connected with the roller while placing the two a position between the light emitter and the light receiver for enabling the light grating to allow/block light emanating from the light emitter to pass therethrough, the continuity of light is measured by the optical sensor so as to determine whether the stethoscope head module is in the auscultation mode basing on the continuity measurement.

9. A stethoscope, adapted for receiving audio signals originated from visceral organs of a living body, comprising:

a stethoscope head module, configured with a sensor and a visceral sound receiver in a manner that the sensor is designed to issue an activation signal as soon as it detects that the stethoscope head module enters an auscultation mode, and the visceral sound receiver is used for receiving the audio signals originated from the visceral organs of the living body;

at least two supporting parts, for positioning the stethoscope in multiple poses, each supporting part comprising:

an earpiece positioned to the top thereof, fitted with at least a second sensor embedded in the earpiece for sensing pressure variations of the earpiece and issuing a second activation signal to the processing unit upon evaluation of the sensed pressure variation to determine whether the stethoscope is ready for entering the auscultation mode;

a joint of the at least two supporting parts, for joining the two supporting parts together, comprising at least a third sensor for detecting the multiple poses of the stethoscope and issuing a third activation signal to the processing unit upon detection of a pose of the stethoscope indicating the stethoscope is ready for entering the auscultation mode;

a preamplifier matching circuit, electrically connected to the stethoscope head module, for amplifying the received audio signals of the visceral organs;

a processing unit, electrically connected to the preamplifier matching circuit, for processing the received audio signals of the visceral organs, comprising:

an audio signal processor, electrically connected to the visceral sound receiver, for processing the received audio signals of the visceral organs and issuing a shut-off signal as soon as the visceral sound receiver receives no visceral sound; and a micro control unit, electrically connected to the sensors, the preamplifier matching circuit, and the audio signal processor, being designed to receive the activation signals and the shut-off signal so as to perform one action selected from the group consisting: turning on the stethoscope according to the activation signal and shutting off the stethoscope according to the shut-off signal;

an attribute visceral sound processor, electrically connected to the processing unit, for receiving and amplifying a characteristic band of the visceral organs contained in the received audio signals;

an audio power amplifier, electrically connected to the attribute visceral sound processor, for amplifying the audio signals of the visceral organs after they are processed by the attribute visceral sound processor; and a signal output unit, electrically connected to the audio power amplifier, for outputting the audio signals received from the audio power amplifier.

10. The stethoscope of claim 9, wherein the audio signal processor is a digital signal processing (DSP) audio signal processor.

11. The stethoscope of claim 9, wherein at least one of the first sensor, the second sensor, and the third sensor is a device selected from the group consisting: a vibration sensor, an accelerometer, an angular velocity sensor, an angle sensor, a pressure sensor, an optical sensor, and the combinations thereof.

12. A stethoscope, adapted for receiving audio signals originated from visceral organs of a living body, comprising:
 a stethoscope head module, configured with an ear hook, at least a first sensor and a visceral sound receiver in a manner that the first sensor is designed to issue an activation signal as soon as it detects that the stethoscope head module enters an auscultation mode and the visceral sound receiver is used for receiving the audio signals originated from the visceral organs of the living body;
 a processing unit, electrically connected to the stethoscope head module to be used for processing the received audio signals of the visceral organs, further comprising:
  an audio signal processor, electrically connected to the visceral sound receiver, for processing the received audio signals of the visceral organs and issuing a shut-off signal as soon as the visceral sound receiver receives no visceral sound; and
  a micro control unit, electrically connected to the sensor and the audio signal processor, being designed to receive the activation signal and the shut-off signal so as to perform one action selected from the group consisting: turning on the stethoscope according to the activation signal and shutting off the stethoscope according to the shut-off signal; and
 a signal output unit, electrically connected to the processing unit and used for outputting the audio signals;
 wherein the ear hook further comprises:
  two supporting parts, joined with each other by an end in a manner that the supporting parts can be positioned as a first pose by pulling the two apart from each other, or can be positioned as a second pose by drawing the two close to each other, both centering around the joint of the two;
  an earpiece positioned to the top thereof, fitted with at least a second sensor embedded in the earpiece for sensing pressure variations of the earpiece and issuing a second activation signal to the processing unit upon evaluation of the sensed pressure variation to determine whether the stethoscope is ready for entering the auscultation mode; and
  at least a third sensor, disposed at the joint of the two-supporting parts in a manner that the at least one sensor is turned on/off according to whether the two supporting parts is positioned as the first/second poses and issuing a third activation signal to the processing unit upon detection of a pose of the stethoscope indicating the stethoscope is ready for entering the auscultation mode.

13. The stethoscope of claim 12, wherein the audio signal processor is a digital signal processing (DSP) audio signal processor.

14. The stethoscope of claim 12, wherein the signal output unit is substantially an earpiece.

15. The stethoscope of claim 12, wherein the stethoscope further comprises:
 a preamplifier matching circuit, electrically connected to the processing unit and the stethoscope head module for amplifying the received audio signals of the visceral organs.

16. The stethoscope of claim 12, wherein the stethoscope further comprises:
 an attribute visceral sound processor, electrically connected to the audio signal processor and the signal output unit, for amplifying a characteristic band contained in the received audio signals of the visceral organs.

17. The stethoscope of claim 12, wherein the stethoscope further comprises:
 an audio power amplifier, electrically connected to the processing unit and the signal output unit for amplifying the audio signals of the visceral organs after they are processed by the processing unit while feeding the amplified audio signal to the signal output unit to be outputted therefrom.

18. The stethoscope of claim 12, wherein at least one of the first sensor, the second sensor, and the third sensor is a device selected from the group consisting: a vibration sensor, an accelerometer, an angular velocity sensor, an angle sensor, a pressure sensor, an optical sensor, and the combinations thereof.

19. The stethoscope of claim 12, wherein the third sensor is turned on when the two supporting parts are positioned as the first pose; and the third sensor is turned off when the supporting parts are positioned as the second pose.

20. The stethoscope of claim 12, wherein the third sensor is a device selected from the group consisting: a contact switch, a pressure sensor, a stress sensor, and the combinations thereof.

21. The stethoscope of claim 12, wherein the second sensor is a pressure sensor for detecting pressure variation of the earpiece; and the detected pressure variation is then compared with a threshold value so as to determine whether the stethoscope head module is in the auscultation mode basing on the comparison.

* * * * *